(12) United States Patent
Ojamo et al.

(10) Patent No.: US 7,482,144 B2
(45) Date of Patent: Jan. 27, 2009

(54) METHOD FOR THE PRODUCTION OF XYLITOL

(75) Inventors: Heikki Ojamo, Kirkkonummi (FI); Merja Penttila, Helsinki (FI); Heikki Heikkila, Espoo (FI); Jaana Uusitalo, Espoo (FI); Marja Ilmen, Helsinki (FI); Marja-Leena Sarkki, Kantvik (FI); Maija-Leena Vehkomaki, Espoo (FI)

(73) Assignee: Danisco Sweeteners Oy (FI)

( * ) Notice: Subject to any disclaimer, the term of this patent is extended or adjusted under 35 U.S.C. 154(b) by 126 days.

(21) Appl. No.: 10/341,220

(22) Filed: Jan. 13, 2003

(65) Prior Publication Data

US 2004/0014185 A1 Jan. 22, 2004

Related U.S. Application Data

(63) Continuation-in-part of application No. PCT/FI01/00663, filed on Jul. 11, 2001.

(60) Provisional application No. 60/217,926, filed on Jul. 13, 2000.

(51) Int. Cl.
*C12P 7/18* (2006.01)
*C12N 7/16* (2006.01)
*C12N 1/18* (2006.01)

(52) U.S. Cl. ............... 435/155; 435/158; 435/105; 435/254.2; 435/254.11

(58) Field of Classification Search .............. None
See application file for complete search history.

(56) References Cited

U.S. PATENT DOCUMENTS 5,631,150 A * 5/1997 Harkki et al. ............ 435/105
5,837,515 A 11/1998 Suominen et al.
6,271,007 B1 * 8/2001 Apajalahti et al. ......... 435/137

FOREIGN PATENT DOCUMENTS

WO WO 93/01299 1/1993
WO WO 95/33063 12/1995

OTHER PUBLICATIONS

La Grange et al. Expression of Trichoderma reesei beta-xaylanase gene (XYN2) in *Saccharomyces cerevisiae* Mar. 1996 vol. 62, No. 3 p. 1036-1044.*
Margolles-Clark (Molecular characterization of side chain cleaving hemicellulases of Trichoderma reesei, Technical Research Center of Finland, Dissertation).*
Kristufek et al (Coinduction od alpha-L-arabinofuranosidase and alpha-D-galactosidase formation in Trichoderma reesei RUT C-30. FEMS Microbiology Letters 115 (1994) 259-264.*
Witteveen C.F.B. et al., "L-Arabinose and D-Xylose Catabolism in *Aspergillus niger*", Journal of General Microbiology 135:2163-2171 (1989).
Chang and Knight, "L-Arabinose Metabolism by Cell-Free Extratcts of *Penicillium chrysogenum*" Biochimica Et Biophysica Acta 46:271-278 (1961).

* cited by examiner

*Primary Examiner*—Rebecca E. Prouty
*Assistant Examiner*—Kagnew Gebreyesus
(74) *Attorney, Agent, or Firm*—Scully, Scott, Murphy & Presser, P.C.

(57) ABSTRACT

The invention relates to a method for the production of xylitol, the method comprising
 (a1) providing (i) a microorganism having xylanolytic activity, and (ii) a microorganism capable of converting a pentose sugar to xylitol; or
 (a2) providing a microorganism having xylanolytic activity and being capable of converting a pentose sugar to xylitol,
 (b) culturing the microorganism of step (a1) (i) or the microorganism of step (a2) in a medium comprising polymer or oligomer materials containing pentose sugars in conditions sufficient for enabling hydrolysis of said polymers or oligomers by the microorganism;
 (c) producing xylitol in the microorganism of step (a1) (ii) or in the microorganism of step (a2) by bioconversion of the hydrolysis products obtained in step (b), and
 (d) recovering said xylitol produced.

Figure 1:
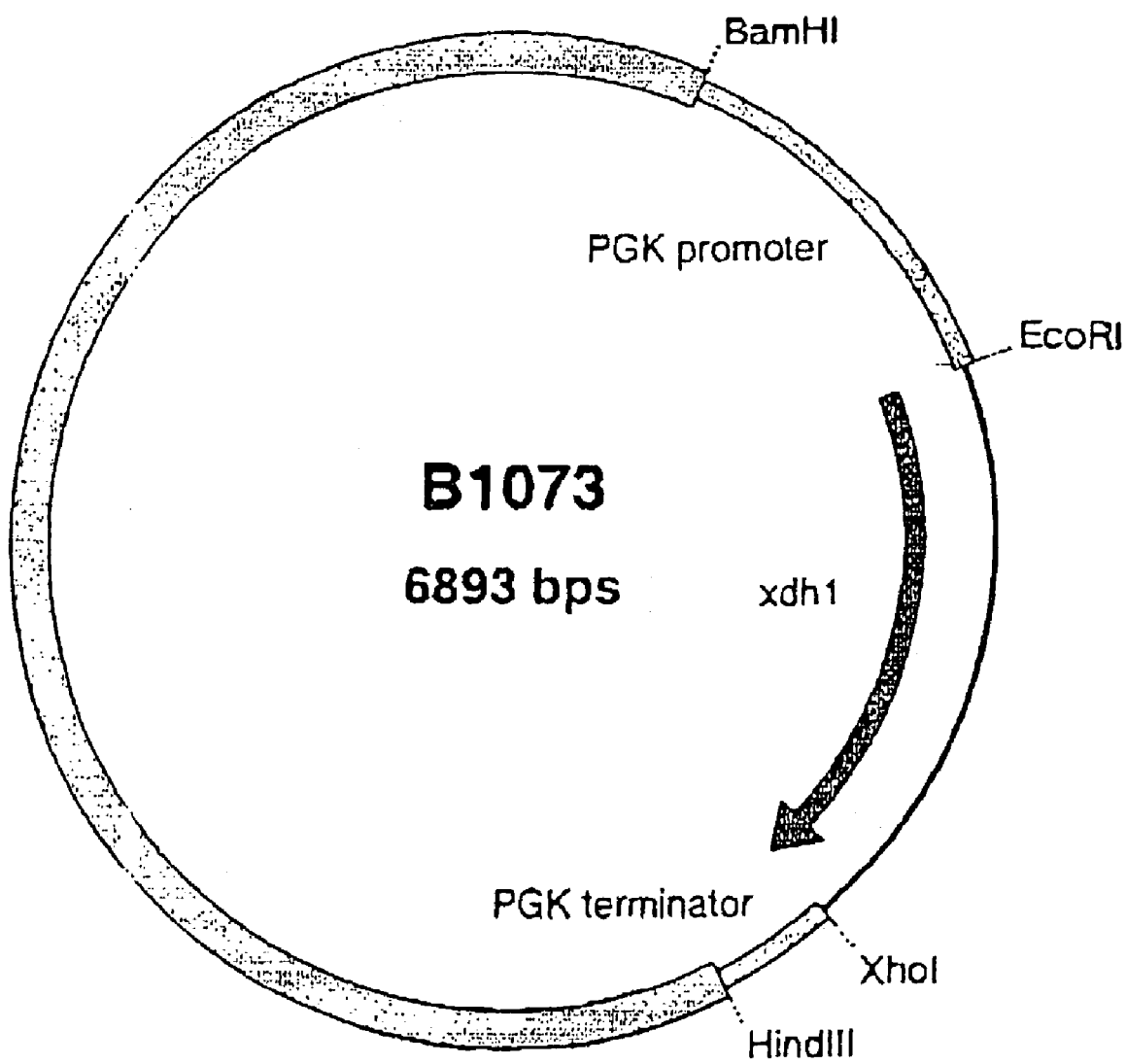

The invention also relates to a microorganism, which has xylanolytic activity and has been genetically modified (i) to enhance its xylanolytic activity, and (ii) to reduce its xylitol metabolism.

13 Claims, 3 Drawing Sheets

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic

<400> SEQUENCE: 1
gaagcttgca tgctctagag gtacc                                    25

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic

<400> SEQUENCE: 2
tcgaggtacc tctagagcat gcaagcttct gca                                33

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Synthetic

<400> SEQUENCE: 3
cggaattccg ggatccggtg aataacgcag ctcttctcgc cgccctg                 47

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic

<400> SEQUENCE: 4
gctctagagc gagctcctcg agggtgaaga gcgagatgag                         40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic

<400> SEQUENCE: 5
cggaattccg aagcttgagt ttgagttggt gggagaagag                         40

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic

<400> SEQUENCE: 6
gctctagagc ggatcccgca atggcaaaaa tggtttgcaa acagaaaact atg          53

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic

<400> SEQUENCE: 7
acatgcatgc atgcggccgc ggtttgttgc cgtaaccatt ctgtctcct               49

<210> SEQ ID NO 8
<211> LENGTH: 48
<212> TYPE: DNA
<213> ORGANISM: Artificial Sequence -continued

```
<220> FEATURE:
<223> OTHER INFORMATION: Description of Artificial Sequence: Synthetic

<400> SEQUENCE: 8
gctctagagc ggatccatgg tgcaatacac agagggtgat cttacaag                48
```

METHOD FOR THE PRODUCTION OF XYLITOL

CROSS-REFERENCE TO RELATED APPLICATIONS

This application is a continuation-in-part application of International Application No. PCT/FI01/00663, filed Jul. 11, 2001, which claims benefit of U.S. Provisional Application Ser. No. 60/217,926, filed Jul. 13, 2000.

FIELD OF THE INVENTION

The invention relates to utilisation of microorganisms in industrial processes for the production of xylitol. In particular, the invention relates to genetic modification of microorganisms in order to enhance their potential as xylitol producers, and to a process for the production of xylitol using said microorganisms.

BACKGROUND OF THE INVENTION

Xylitol is usually prepared by processes in which a xylan-containing material is first hydrolysed to produce a mixture of monosaccharides, including xylose. The xylose is then converted to xylitol, generally in a chemical process using a nickel catalyst such as Raney-nickel. A number of processes of this type have been described in the literature of the art. U.S. Pat. No. 3,784,408 (Jaffe et al.), U.S. Pat. No. 4,066,711 (Melaja et al.), U.S. Pat. No. 4,075,406 (Melaja et al.), U.S. Pat. No. 4,008,285 (Melaja et al.) and U.S. Pat. No. 3,586,537 (Steiner et al.) may be mentioned as examples.

Alternatively, xylitol can be produced from glucose. U.S. Pat. No. 5,096,820, Leleu et al., describes a process in which D-glucose is microbiologically converted to D-arabitol, which likewise is microbiologically converted to D-xylulose. The D-xylulose is then enzymatically isomerised into a mixture of D-xylose and D-xylulose, which is catalytically hydrogenated. Finally, the xylitol is recovered by chromatographic separation or crystallisation. U.S. Pat. No. 5,238,826, Leleu et al., uses a similar process to obtain xylose, ultimately for the preparation of xylitol by hydrogenation. The xylose is produced by microbiological conversion of D-glucose via D-arabitol to D-xylulose, which is then enzymatically isomerised into a mixture of D-xylose and D-xylulose. Finally, the mixture is subjected to chromatographic separation, the D-xylose fraction is recovered and the D-xylulose fraction is recirculated into the isomerisation step.

These prior methods are, however, technically complicated multistep processes which have relatively low efficiency. The greatest problems reside in achieving an effective and complete separation of xylose from other hydrolysis by-products. Thorough purification is essential, because the catalysts used in the reduction reaction of xylose are very sensitive. As regards the purity of the final product, the separation of xylitol from the other products produced in the reduction reaction will greatly depend on the amount of other components present. The more components, the more complicated and time-consuming purification and separation processes will be needed. Altogether, the production of xylitol by these processes is very costly.

Several attempts to utilise microorganisms for the biotechnological production of xylitol have also been reported. A main advantage of using microorganisms is that they are not as susceptible to varying reaction conditions as chemical catalysts. The production of xylitol by means of a biotechnological process is thus a highly attractive alternative, provided that such processes are able to provide a high quality product by a comparatively cost-effective method.

It is known that many yeast strains produce reductase enzymes that catalyse the reduction of sugars to corresponding sugar alcohols. Many yeasts, in particular *Pichia, Candida, Hansenula* and *Kluyveromyces*, are also capable of reducing xylose to xylitol as an initial step in their xylose metabolism, and several yeast strains are able to use xylose as a sole source of carbon and energy.

The reaction route or pathway of xylose utilisation for yeasts is in general the following: xylitol is synthesised in the first step by reduction of xylose to xylitol with the aid of xylose reductase. Xylitol is then metabolised by a series of successive steps. Xylitol is first oxidised to xylulose with xylitol dehydrogenase, xylulose is phosphorylated to xylulose-5-phosphate with xylulose kinase (also called xylulokinase), and then part of the xylulose-5-phosphate is converted to pyruvate via several intermediate steps. Also ethanol and $CO_2$ can be formed. The relevant main products and by-products vary depending on the yeast strain and the fermentation conditions. The reactions are not tightly coupled, and consequently, some xylitol is often accumulated.

It has also been reported that some bacteria, such as *Corynebacterium* sp. and *Enterobacter liquefaciens*, produce xylitol by the same pathway, utilising xylose as the main metabolite. However, the yields obtained have been very poor. So far, only one species of filamentous fungus, *Petromyces albertensis*, has been shown to produce notable amounts of xylitol from xylose [Winkelhausen E. and Kuzmanova S., *J. Ferment. Bioeng.* 86:1-14 (1998)]. Hence, prior to the present invention, there has been no incentive to use bacteria or filamentous fungi for xylitol production.

Also as regards yeasts, the research has generally focused on attempts to identify yeast strains with enhanced ability to produce ethanol rather than xylitol. Nevertheless, xylitol production is relatively common among xylose-utilizing yeasts. For example, of 44 yeasts belonging to five different genera, *Candida, Hansenula, Kluyveromyces, Pichia* and *Pachysolen*, 42 produced some xylitol into the culture media [Barbosa. M. F. S. et al., *J. Indust. Microbiol.* 3241-3251 (1988) and *Enzyme Microb. Technol.* 10:66-81 (1988)].

It has been suggested to use such strains for the industrial production of xylitol. PCT publications WO 90/8193, WO 91/0740, WO 88/5467 and French published application 2 641 545 describe the use of *Candida tropicalis, Candida guilliermondii* and *Candida parapsilosis*, respectively.

U.S. Pat. No. 5,081,026, Heikkilä et al., describes a process for the production of xylitol from xylose, in which an aqueous xylose solution is fermented with a yeast strain capable of converting free xylose to xylitol and free hexoses to ethanol. After fermentation, a xylitol-rich fraction is obtained by chromatographic separation, and finally, xylitol is recovered from said fraction. In particular *Candida* and *Debaryomyces* are mentioned as suitable yeast species.

Profitable industrial production of xylitol by enzymatic bioconversion of xylose is possible only if the yield is high. No wild yeast strains have been shown to achieve this.

An attempt to solve this problem has been described in WO 91/15588, Hallborn, J. et al. The inventors cloned the xylose reductase gene from *Pichia stipitis* into *Saccharomyces cerevisiae* and obtained strains capable of converting xylose into xylitol with a claimed yield of 95% [Hallborn et al., *Bio/Technology* 9:1090 (1991)]. *Saccharomyces cerevisiae* does not normally express enzymes of the xylose pathway, but is widely accepted and commonly used in the food industry for other purposes, for example in bakery.

Gong C. et al., *Biotechnol. Letters* 3:125-130 (1981) describe two high xylitol producing yeast mutants denominated HXP 1 and HXP 2, obtained after UV-mutagenesis of a wild strain of *Candida tropicalis* which originally was capable of metabolising D-xylose into xylitol.

Mutants defective in xylose utilisation have also been described. Hagedorn J. et al., *Curr. Genetic.* 16:27-33 (1989) disclose mutants of the yeast *Pichia stipitis* which were unable to utilise xylose as the sole carbon source and which were deficient in either xylose reductase or xylitol dehydrogenase. Stevis, P. E. et al., *Appl. Biochem. Biotechnol.* 20:327-334 (1989) disclose the construction of yeast xylulokinase mutants by recombinant DNA techniques.

EP 0 604 429, Xyrofin, describes novel yeast strains with modified xylitol metabolism, a process for the production of said strains, and the use of said strains in a process for producing xylitol. The strains are capable of reducing xylose into xylitol, but are deficient in one or more enzymes involved in the xylitol metabolism, with the effect that the xylitol produced accumulates in the culture medium and can be recovered therefrom. The yeasts described belong to the genera *Candida*, *Hansenula*, *Kluyveromyces* or *Pichia*, and the genetic modification eliminates or reduces expression of the gene that encodes xylitol dehydrogenase or xylulose kinase, or both.

EP 0 672 161, Xyrofin, describes a method for the production of xylitol from carbon sources other than xylose and xylulose by using recombinant hosts. The microorganisms either produce xylitol via an altered arabitol route involving in particular arabitol dehydrogenase, or via altered (over) expression of genes encoding the enzymes of the oxidative branch of the pentose phosphate pathway (PPP), in particular glucose-6-phosphate dehydrogenase or 6-phospho-D-gluconate dehydrogenase, thus enabling utilisation of glucose, for instance. When used, D-glucose is phosphorylated into D-glucose-6-phosphate and converted to D-ribulose-5-phosphate via 6-phospho-D-gluconate. The D-ribulose-5-phosphate is then epimerised to D-xylulose-5-phosphate, dephosphorylated to D-xylulose and reduced to xylitol. Amplification of glucose-6-phosphate dehydrogenase enzyme activity in osmotolerant yeasts is also described in FR 2 772 788, Roquette Freres.

EP 0 974 646 A describes microorganisms capable of producing xylitol, or xylulose, from glucose. The microorganisms are naturally occurring and belong to the family Acetobacteracea. Novel strains of genus *Asaia* and *Zucharibacter* are mentioned as preferred.

Another approach that could be taken in the bioproduction of xylitol is the enhancement of xylose production, thus providing more xylose as the primary metabolite for xylitol production.

Some fungi, including *Aureobasidium*, *Aspergillus*, *Trichoderma*, *Fusarium* and *Penicillium*, have been reported to have xylanolytic activity and thus be able to degrade xylan-containing biopolymers and metabolise the xylan into xylose. In addition, several yeast species have been thoroughly studied, but their hydrolytic activity has not been the main target for the studies and has not been applied in large-scale industrial processes.

Kuhad R. C. et al., *Process Biochemistry* 33:641-647 (1998) describe a hyperxylanolytic mutant strain of *Fusarium oxysporum* produced by UV and N-methyl-N'-nitro-N-nitrosoguanidine (NTG) treatment, and the enhancement of its xylanase production by optimisation of several nutritional and fermentation parameters, including temperature, pH, substrate and inoculum size.

Some *Trichoderma* strains have also been shown to be efficient producers of hemicellulases, in particular xylanase. The literature of the art also includes several reports on attempts to provide induction of β-xylosidase production during fermentation. Kristufek D. et al., *Appl. Microbiol. Biotechnol.* 42:713-717 (1995), using xylose, xylobiose and xylan as inducers for β-xylosidase induction in *Trichoderma reesei*, and Margolles-Clark E. et al., *J. Biotechnol.* 57:167-179 (1997), studying the expression of ten hemicellulase-encoding genes and using e.g. cellulose, xylobiose, xylan and L-arabitol as inducers, may be mentioned as examples.

The enhancement of hemicellulase activity by various gene manipulation techniques have also been reported. For instance Margolles-Clark E. et al., *Appl. Environ. Microbiol.*, October 1996, 3840-3846, describe the isolation of the genes encoding β-xylosidase and α-L-arabinofuranosidase from *Trichoderma reesei* and cloning and expressing said genes in *Saccharomyces cerevisiae*. WO 97/00964, Rijksland-Bouwuniversiteit Wageningen, describes a novel β-xylosidase from *Aspergillus niger*, the nucleotide sequence encoding it and its use especially as a bread improver. *Aspergillus*, *Trichoderma* and *Fusarium* are mentioned as host cells. Hodits R. et al., *ECB6: Proceedings of the 6$^{th}$ European Congress on Biotechnology*, 13$^{th}$ to 17$^{th}$ June 1993, report on recombinant *Trichoderma reesei* strains producing improved and tailor-made xylanases, including a method of amplifying a gene encoding β-xylosidase. U.S. Pat. No. 5,837,515, Nevalainen et al., discloses a method for overproduction of hemicellulases, including endoxylanase, β-xylosidase, α-arabinosidase, α-D-glucuronidase and acetyl esterase, by cultivating *Trichoderma reesei* strains at least partially deficient in expressing cellulase enzyme(s) and transformed to include multiple copies of the gene encoding the desired enzyme(s).

Also bacteria have been studied in this respect. As an example may be mentioned Paice et al., *Biotechnology and Bioengineering* 32:235-239 (1988) describing in the article "Viscosity-enhancing bleaching of hardwood kraft pulp with xylanase from a cloned gene" *Escherichia coli* strains capable of overproduction of endoxylanase and β-xylosidase. For instance some *Bacillus* and *Clostridium* strains have also been reported to have xylanolytic activity.

The background art thus describes the production of xylitol from xylan by multistep chemical processes or by multistep combinations of chemical and biological processes. Further, processes utilising microorganisms, in particular yeasts, capable of producing xylitol from monosaccharide solutions or pure xylose solutions have been described. So far, no industrial processes for the production of xylitol from complex xylan-containing materials solely by means of a biotechnological method have been described, despite the fact that such a process would offer several advantages as compared to conventional processes, as far as efficient utilisation of the raw material and efficient production of xylitol in a cost-effective manner is concerned. There thus remains a constant need for further research and development in this area, with the aim of achieving efficient bioproduction of xylitol.

SUMMARY OF THE INVENTION

The present invention is based on a novel and inventive combination of two features: it combines utilisation of xylanolytic activity with restricted or inhibited xylitol metabolism.

In one main embodiment of the invention, two microorganisms are used for the production of xylitol, one microorganism possessing xylanolytic activity and the other possessing the enzymatic activity needed for conversion of a pentose sugar, such as xylose and arabinose, preferably xylose, to xylitol.

In a preferred embodiment of the invention, the xylanolytic microorganism is a mold.

In another preferred embodiment, the microorganism possesses enhanced xylanolytic activity as a result of being genetically modified.

The microorganism responsible for the enzymatic conversion of a pentose sugar, such as xylose and arabinose, preferably xylose to xylitol is, preferably, a yeast. In a preferred embodiment of the invention, said microorganism has reduced ability to metabolise xylitol.

In one embodiment of the present invention, the reduced ability to metabolise xylitol is a result of genetically modifying the expression of one or more enzymes participating in the xylitol metabolism to reduce said metabolism in said microorganism. Alternatively, a microorganism can be used which in its natural form does not produce xylitol, or produces xylitol via a different pathway not utilising xylose as the main metabolite, and in which the necessary pathways have been introduced by genetic engineering.

For the production of xylitol, the two microorganisms can be used simultaneously or successively or separately. Simultaneous production of both xylose and xylitol is regarded as preferred, due to less inhibitory activity, especially on the xylose production by accumulated xylose.

In the other main embodiment of the invention, one microorganism, possessing both xylanolytic activity and the enzymatic activity needed for the conversion of xylose to xylitol, is used.

Preferably, the microorganism is a mold or a yeast. More preferably a xylanolytic microorganism is used, which has been genetically modified to cause overproduction of the xylanolytic activity and reduced ability to metabolise xylitol.

Also in this embodiment of the invention, it is possible to use a microorganism which lacks xylanolytic activity in its natural form but in which genes encoding xylanolytic activity have been introduced. In a corresponding manner, it is also possible to use a microorganism which in its natural form does not produce xylitol, or produces xylitol via a different pathway, and introduce the necessary pathways by genetic engineering.

In the process, varying amounts of ethanol can also be produced. If the pathway(s) for utilisation of xylitol in the microorganism are completely blocked, very small amounts of ethanol are produced, if any. However, when the xylitol metabolism is restricted only to a certain degree, varying amounts of ethanol are formed and can be recovered during the process.

The invention thus relates to a method for the production of xylitol, the method comprising (a) providing (i) a microorganism having xylanolytic activity, and (ii) a microorganism capable of converting a pentose sugar to xylitol;

(b) culturing the microorganism of step (a) (i) in a medium comprising polymer or oligomer materials containing pentose sugars in conditions sufficient for hydrolysis of said polymers or oligomers;

(c) producing xylitol in the microorganism of step (a) (ii) by bioconversion of the hydrolysis products obtained in step (b), and (d) recovering said xylitol produced.

The invention further relates to a method for the production of xylitol, the method comprising (a) providing a microorganism having xylanolytic activity and being capable of converting a pentose sugar to xylitol, (b) culturing the microorganism of step (a) in a medium comprising polymer or oligomer materials containing pentose sugars in conditions sufficient for enabling hydrolysis of said polymers or oligomers by the microorganism;

(c) producing xylitol in the microorganism of step (a) by bioconversion of the hydrolysis products obtained in step (b), and (d) recovering said xylitol produced.

The invention also relates to genetically modified novel microorganisms which have xylanolytic activity and enhanced xylitol production as compared to the corresponding wild-type microorganisms, due to reduced ability to metabolise xylitol. In a preferred embodiment, the microorganism also has enhanced ability to produce xylose as a starting material for xylitol production.

In particular, the microorganism has xylanolytic activity and has been genetically modified to enhance its xylanolytic activity and reduce its xylitol metabolism.

The invention further relates to a process for the production of said genetically modified microorganism, said process comprising (i) providing a xylanolytic microorganism;

(iia) modifying the expression of one or more enzymes participating in the xylitol metabolism to reduce said metabolism in said microorganism; and optionally (iib) modifying the expression of one or more enzymes participating in the xylanolytic activity to enhance said xylanolytic activity in said microorganism.

DRAWINGS

Figure 2:
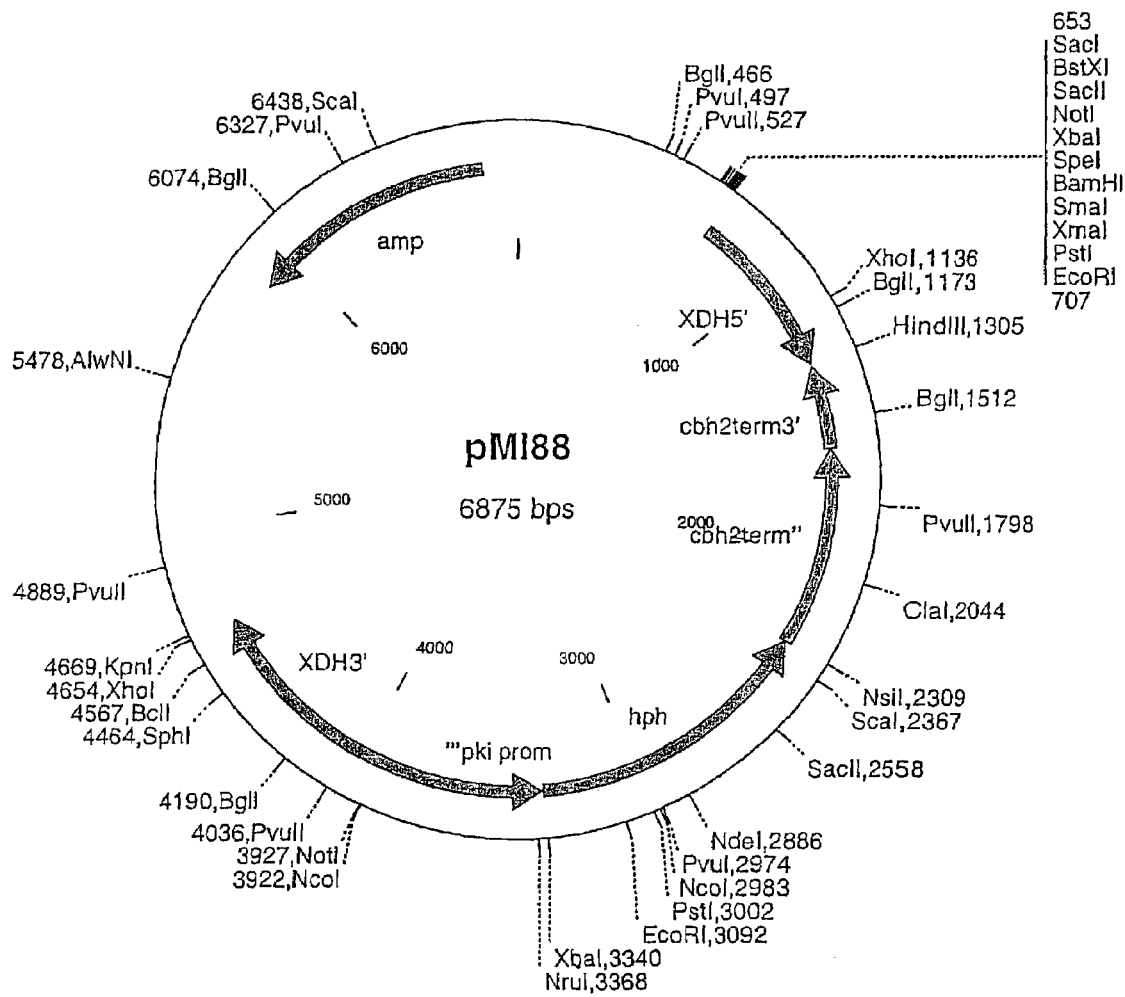
Figure 3:
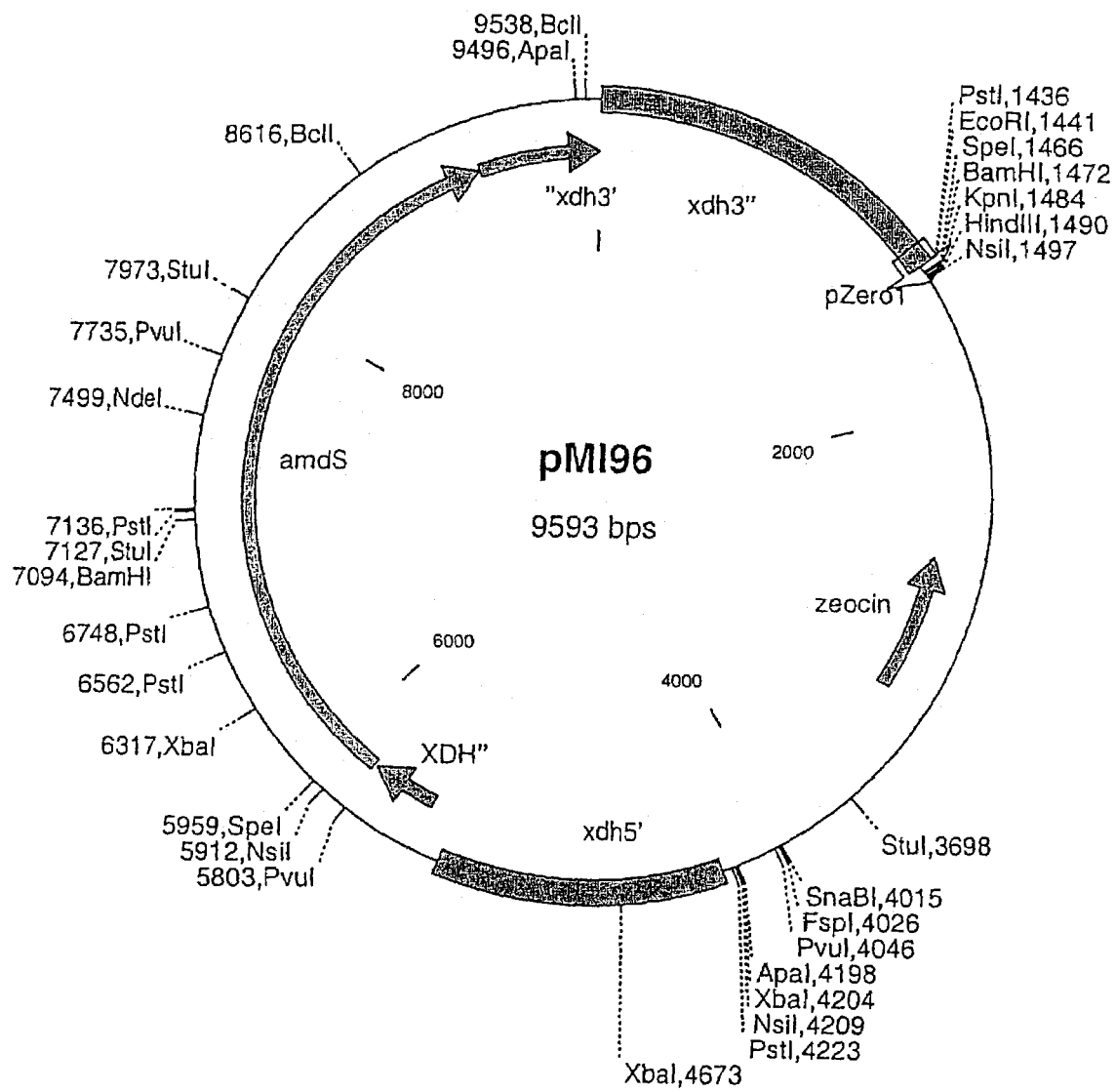

FIG. 1 illlustrates the structure of plasmid B1073.
FIG. 2 illustrates the construction of plasmid pM188.
FIG. 3 illustrates the construction of plasmid pM196.

DETAILED DESCRIPTION OF THE INVENTION

The basis for the present invention is the unique concept of using one or more microorganisms having both xylanolytic activity and ability to convert a pentose sugar, such as xylose or arabinose, preferably xylose, to xylitol, either in combination or separately, for xylitol production. In particular, the invention uses xylanolytic microorganisms which due to genetic modification show overproduction of xylanolytic activity and blocked or reduced xylitol metabolism.

Thus, in accordance with the present invention, the production microorganism has xylanolytic activity and can hydrolyse pentose-sugars-containing materials into metabolisable forms of pentose sugars. Furthermore, it preferably comprises at least one genetic modification leading to enhanced xylanolytic activity as compared to a corresponding unmodified organism. The present invention also utilises a microorganism having the ability to convert a pentose sugar, such as xylose or arabinose, preferably xylose, to xylitol and preferably comprising at least one genetic modification leading to reduced capability to metabolise xylitol as compared to a corresponding unmodified organism. Preferably, one and the same microorganism includes both types of genetic modification.

Lignocellulosic materials are very abundant in nature and offer both renewable and cheap carbohydrate sources for microbial processing. The major components in lignocellulosic materials are cellulose, hemicellulose and lignin, the amounts and proportions of which vary with plant species. The hemicellulose portion of plant cell walls contains as a major component xylan, constituting up to 35% of the total dry weight. β-D-xylo-pyranose units linked with a 1-4 glycosidic bond form the main chain of D-xylans. Pure D-xylan, formed from D-xylose alone, occurs rarely, and most D-xylan structures have other sugars as side chains. One of the common side chains is L-arabinose, which in most cases is in the form of furanose. L-arabinose often forms the side chain alone, even though the chain may even comprise a plurality of sugar groups. In different plants, the proportion of L-arabinose and D-xylose varies greatly, depending on how branched said molecule is. The homopolymeric backbone chain of beta-1,4-linked D-xylose units in xylan may also carry short side chains containing e.g. glucuronic acid or its O-methyl-ether, acetic acid, coumaric acid and ferulic acids. Lignocellulosic materials thus contain a complexity of sugars with glucose as the main hexose and xylose as the main pentose, and with arabinose, mannose and galactose as minor components. Hemicellulosic materials also comprise several monosaccharides, xylose usually being the main component and arabinose, glucose, mannose and galactose being minor components. For example, in soft wood, mannose is the main component of the hemicellulosic material. In addition to by-products from paper and pulp industry, such as spent liquor and wood hydrolysates, also agricultural by-products, such as sugar bagasse, corn cobs, corn fiber, oat, wheat, barley and rice hulls and straw and hydrolysates thereof contain high amounts of pentosans, and can be utilised as starting materials in the present invention. As starting material, arabane or galacturonic acid containing polymeric materials can also preferably be utilised.

One of the advantages of the present invention is the possibility to use these abundant sources of xylan-containing biomass for the production of xylose to be further metabolised to xylitol. This advantage is achieved by using a microorganism having xylanolytic activity in accordance with the present invention.

The raw material may be pretreated before use when appropriate. Suitable pretreatment methods include hydrolysis, steam explosion and separation techniques. For instance when wood is utilised as the starting material, it is preferably ground into chips, sawdust, shavings and the like, and subjected to hydrolysis, or steam explosion and hydrolysis. Before fermentation it may also be appropriate to remove constituents which may be toxic or otherwise harmful to the microorganism used, or which may interfere with subsequent separation and/or purification steps. Preferably, the raw material is dissolved, or converted into a dissolved form, upon use.

In connection with the present invention, "xylanolytic activity" means any enzymatic activity capable of catalysing the breakdown of hemicelluloses, pentosan-containing material and xylan-containing material, including e.g. pentosanases, xylanases, such as 1,4-beta-D-xylanohydrolase, hemicellulases, glycosidases, xylosidases, such as β-xylosidase, arabinosidases and arabinanases, glucuronidases, acetylxylan esterases, ferulic acid esterases, coumaric acid esterases, mannanases and mannosidases, galactanases and galactosidases, rhamnosidases, galacturonidases. The most important enzyme activities in the utilisation of xylan and/or xylo-oligosaccharide containing plant-derived materials are those performed by endoxylanases and β-xylosidases, the other activities being mainly auxiliary in nature.

The xylanolytic microorganism used in the present invention can be any microorganism which comprises xylanolytic activity, either as an inherent or added property.

Suitable microorganisms can be found among species belonging to fungi, i.e. yeasts and molds, and bacteria. As examples may be mentioned e.g. *Trichoderma, Aspergillus, Aureobasidium, Pichia, Candida, Debaryomyces, Hansenula, Kluyveromyces, Pachysolen, Saccharomyces, Schizosaccharomyces, Fusarium, Streptomyces, Bacillus* and *Clostridium*. In the context of the present invention, yeasts and filamentous fungi are regarded as preferred microorganisms. In view of its excellent xylanolytic activity, *Trichoderma* sp., and in particular *Trichoderma reesei* and *Trichoderma longibrachiatum*, are regarded as most preferred. As regards the alternative process for production of both xylitol and ethanol, *Fusarium* sp., in particular *Fusarium oxysporum*, can be mentioned as preferred.

Within the framework of the present invention it is possible, as already mentioned, to use microorganisms which lack xylanolytic activity in their natural form but in which genes encoding xylanolytic activity have been introduced.

In accordance with the present invention, the xylanolytic microorganism preferably contains a metabolic modification which results in overexpression of xylanolytic activity.

The xylanolytic activity can be enhanced by a number of modifications, such as overexpression of β-xylosidase and other hemicellulolytic activities. Overexpression can be achieved both by introducing multiple copies and amplification of the microorganism's homologous genes, by introducing heterologous genes and by altering the regulation of the expression of the genes. Examples of genes encoding xylanolytic activity and appropriate for use in the present invention include, but are not limited to, β-1,4-xylanohydrolase, β-xylosidase, α-arabinofuranosidase and arabinanase.

Overexpression of the microorganism's homologous genes encoding β-xylosidase is regarded as the most preferred embodiment.

Also the xylitol metabolism can be altered in a multitude of ways. By using a xylanolytic microorganism one can assure that more xylose is available for further metabolism into xylitol, and thereby the amount of xylitol produced will be higher. Enhanced production of xylitol is very likely to lead to accumulation of xylitol into the cell, and enhanced secretion of xylitol from the cell is easily accomplished. An even more efficient measure is naturally to hamper the xylitol metabolism and thus reduce or prevent loss of xylitol produced. This can be made by inactivating, blocking, deleting or otherwise modifying the enzyme activities responsible for the further utilisation of xylitol by the cell, either on enzyme level or by acting directly on the genes encoding the enzyme activities, for instance by altering the substrate specificity cofactor requirements, or specific activity, by protein engineering. As appropriate targets for such modifications may be mentioned xylitol dehydrogenase and xylulokinase.

As already mentioned, it is also possible to introduce a xylitol producing pathway in organisms lacking such, for instance by introducing xylose reductase and permease, or L-arabinose reductase, arabinitol dehydrogenase (L-xylulose forming) and L-xylulose reductase genes into such an organism. In cases where the microorganism includes an alternative pathway for xylitol production, this can be blocked, when appropriate. For the purpose of producing xylitol in accordance with the present invention, the xylitol dehydrogenase gene, when present, can also be deleted or blocked.

The xylanolytic microorganism can further be modified in a number of different ways aiming at further intensifying the xylitol production. Such auxiliary modifications include, but are in no way limited to, overexpression of the genes mentioned above.

The genetic modifications can be made using conventional methods for genetic modification, such as those described in Maniatis et al. Molecular cloning. A laboratory manual, Cold Spring Harbor Laboratory, New York 1982.

In a preferred embodiment, the present invention hence utilises a xylanolytic microorganism that has been genetically modified so as to produce more pentose sugars for production of xylitol or alternatively, or in addition, to inhibit further metabolism of the xylitol produced. The microorganism is able to perform all steps needed in the process, by using other sugars for the maintaining of growth, from the hydrolysis of the pentosan-containing oligomers or polymers, via the enhancement of xylose production to the final conversion of xylose to xylitol.

When appropriate, some of the reactions can be carried out chemically, such as by using chemical reduction of arabinose to arabinitol to be further converted, microbiologically or otherwise, to xylulose and finally to xylitol and arabinitol. Another possibility is, for instance, to utilise araban, arabinoxylan or a mixture of araban and xylan as starting material. The starting material can be acid hydrolyzed into a mixture of arabinose and xylose. The mixture is then reduced, microbiologically by use of an appropriate bacterium or yeast, enzymatically or by chemical hydrogenation, yielding a mixture of arabinitol and xylitol. The xylitol is separated and the arabinitol oxidized into xylulose and optionally some arabinitol, which mixture then is chemically hydrogenated into a mixture of arabinitol and xylitol. The xylitol obtained is separated. The processes are preferably combined with recirculation of the obtained arabinitol into the process.

In addition, or alternatively, some of the reaction steps can be further intensified by externally adding suitable microorganisms and other reagents, for instance commercial enzyme products, cofactors and cosubstrates, or hexoses or pentoses in a utilisable form.

The xylitol yield will naturally also depend on the fermentation conditions and the medium used. One of the critical parameters is the availability of necessary coenzymes, in particular pyridine nucleotide cofactors. As other key parameters the substrate concentration and oxygen supply can be mentioned. Also other cofactor, cosubstrate and nutritional requirements, availability of hexose sugars for growth, presence of inducers or inhibitors, temperature and pH, etc., will have a marked influence on the xylitol yield. The optimisation of said parameters may provide better yields than those reported in the present application. The measures required are well-known to persons skilled in the art and will therefore not be described in this context.

As shown in the examples of this document, the use of a nitrogen-free or nitrogen-poor medium can enhance the xylitol yield. This is, consequently, regarded as a preferred embodiment of the invention.

In connection with the present invention it has also been proved, for instance, that by overexpressing the homologous β-xylosidase gene in *Trichoderma reesei*, the β-xylosidase activity could be increased about 15-fold to 450 nkat ml$^{-1}$ as compared to 32 nkat ml$^{-1}$ for the parent strain. The specific β-xylosidase activity was 72.6 nkat g$^{-1}$ protein and 4.9 nkat g$^{-1}$ protein, respectively. By changing the substrate and using appropriate induction, the β-xylosidase activity could be further increased, up to 960 nkat ml$^{-1}$ for the recombinant microorganism of the present invention.

In hydrolysis studies made, it has also been shown that the enzymes produced by the recombinant *T. reesei* strains are the most efficient ones to effect the hydrolysation of xylan-containing raw materials to xylan. For instance the amount of enzyme produced by the microorganisms of the present invention, which is required to hydrolyse 85% of xylo-oligosaccharides into xylose is only about ⅛ of the amount of the enzyme produced by the unmodified host strain.

Altering the xylitol metabolic pathway in accordance with the present invention also led to significant improvement in the final xylitol production. By inactivating the xylitol dehydrogenase (xdh) gene, effecting the conversion of xylitol to xylulose, it was possible to increase the xylitol production up to 10-fold in the transformant as compared to the unmodified parent strain. Adding glucose to the medium used provided more cofactors for the conversion of xylose to xylitol, resulting in one particular study in a xylitol production of 5-5.5 gl$^{-1}$, with the transformant, as compared to 3.1 gl$^{-1}$ without glucose.

By using a strain that has been genetically modified both by enhancing its xylanolytic activity and inhibiting its xylitol metabolism, the xylitol production can be improved even further. Based on the studies made, an increase of 20 times and more can be expected, as compared to the parent strain.

The xylitol produced can be recovered from the fermentation broth by various techniques known per se. Such techniques include for example filtration, ultrafiltration, chromatographic methods, crystallisation etc. When using chromatography, arabinitol-rich fractions obtained can be recycled, and used as a fermentation medium component, i.e. raw material, for further xylitol production. The enzymes produced can be easily recovered from the fermentation broth by ultrafiltration, the retentate containing the enzymes, while the permeate contains e.g. xylitol and arabinitol.

In studies made in connection with the present invention, it has also surprisingly been shown that the inactivation of xylitol dehydrogenase, as an example of an enzyme of the xylitol pathway, does not affect xylitol production in any way. Xylitol production hence occurs normally in the cell. Furthermore, the enhanced amounts of xylitol do not act as inhibitors of further synthesis, which is surprising considering that xylose on the enzyme level is known as an inhibitor of further xylose production [Kersters-Hilderson et al. (1969) European J. Biochem. 7:434-441; Dekker (1983) Biotechnol. Bioeng. 30:1127-1146; Rodionova et al. (1983) J. Appl. Biochem. 5:300-312; Poutanen and Puls. (1988) Appl. Microbiol Biotechnology 28:425-432]. As a further surprising feature it can be mentioned that, in the studies conducted so far, xylitol has not been shown to inhibit xylanolytic activity, either. This is a major benefit of the process.

The methods of the present invention have several advantages as compared to known processes.

Firstly, they enable the utilisation of a wide variety of raw materials. Due to its xylanolytic activity, the microorganism used as a production organism is itself able to hydrolyse even complex xylan-containing raw materials, such as pentose-sugar-containing polymers and oligomers, lignocellulose-based hydrolysates and extracts, pentosans extracted from lignocellulosic materials, bagasse, sugar beet pulp, bran, straw etc. Thus, by using the methods according to the present invention, it is possible to utilise a large variety of raw materials as starting material.

Secondly, the microorganism(s) is(are) capable of carrying out all the necessary reactions, from the hydrolysis of the raw material, via the metabolic conversion of the hydrolysis products, to the desired end product.

Thirdly, the genetic modification of the microorganisms, irrespective of whether it involves overexpression of genes encoding for xylanolytic activity, or blocking or inactivation of genes responsible for the further metabolism of xylitol, or both, leads to enhanced xylose production. The excess of xylose produced by the increased xylanolytic activity of the cells is further metabolised into xylitol, thus leading to enhanced xylitol production. The overall xylitol production rate thus by far exceeds the rate achieved by the use of conventional microorganisms.

The invention will be described in detail in the following specific examples. The examples are included herein for illustrative purposes only and are not to be construed as limiting or restricting the scope of the invention in any way.

As described in the following examples, *E. coli* strain DH5α was used as host in *E. coli* clonings and *Trichoderma reesei* strain RutC-30 (ATCC 56765, VTT-D-86271) [Montenecourt Eveleigh Adv. Chem. Ser. (1979), 289-301] was used in fungal transformation and expression studies.

EXAMPLE 1

Construction of Vectors for Expression of β-xylosidase Under the cbh2- and the gpdA-promoters in *Trichoderma*

1. Cloning of the bxl1 Protein Coding Region

The commercial plasmid pSP73 (Promega) was modified by ligating a linker fragment containing recognition sites for PstI, HindIII, SphI, XbaI, KpnI and XhoI between the PstI and XhoI restriction sites in the multiple cloning region of the plasmid. The multiple cloning region in the plasmid obtained, pSP73 (MLO), contains recognition sites for restriction enzymes BglII, EcoRV, ClaI, EcoRI, SacI, KpnI, SmaI, BamHI, XbaI, SalI, AccI, PstI, HindIII, SphI, XbaI, KpnI, and XhoI.

The linker oligos:

```
                                          (Sequence ID. No. 1)
1. 5' GAAGCTTGCATGCTCTAGAGGTACC 3'
                                          (Sequence ID. No. 2)
2. 5' TCGAGGTACCTCTAGAGCATGCAAGCTTCTGCA 3'
```

The protein coding region of the bxl1 gene was subcloned in three fragments. A SacI+Hind III fragment carrying the middle part of the gene (2047 bp) was isolated from the plasmid p18SA [Margolles-Clark, E. et al., Appl. Environ. Microbiol 62:219-228, 1996)] and inserted into the plasmid pSP73(MLO) between SacI and HindIII. The resulting plasmid was named pMLO130. The 5'-end (252 bp) and the 3'-end (192 bp) were synthesised with PCR using p18SA as a template. PCR products were digested with EcoRI and XbaI and inserted into the plasmid pSP73 and the resulting plasmids now carrying the 3'-end and the 5'-end of the bxl1 coding region were named pMLO131 and pMLO132, respectively. The 3'-end fragment was first sequenced and then isolated from pMLO131 as a Hind III+XbaI fragment and inserted into the plasmid pMLO130 between HindIII and XbaI to obtain plasmid pMLO134. The 5'-end fragment was first sequenced and then isolated from pMLO132 as a EcoRI+SacI fragment and inserted into the plasmid pMLO134 between EcoRI and SacI. The resulting plasmid pMLO135 now carries the whole protein coding region of the bxl1 gene with BamHI restriction sites in both ends.

```
The PCR primers for the cloning of the 5'-end fragment:

EcoRI    BamHI  +bxl1
1. 5' CGGAATTCCGGGATCCGGTGAATAACGCAGCTCTTCTCGCCGCCCTG 3'     (Sequence ID. No. 3)

XbaI    SacI
2. 5' GCTCTAGAGCGAGCTCCTCGAGGGTGAAGAGCGAGATGAG 3'             (Sequence ID. No. 4)

The PCR primers for the cloning of the 3'-end fragment:

EcoRI    HindIII
1. 5' CGGAATTCCGAAGCTTGAGTTTGAGTTGGTGGGAGAAGAG 3'             (Sequence ID. No. 5)

XbaI    BamHI
2. 5' GCTCTAGAGCGGATCCCGCAATGGCAAAAATGGTTTGCAAACAGAAAACTATG 3' (Sequence ID. No. 6)
```

2. Cloning of the cbh2 Promoter of *T. reesei*

A 1000 bp fragment from the 5' non-coding region of the cbh2 gene of *T. reesei* strain QM9414 (ATCC 26921) was synthesised with PCR using total DNA as a template. A plasmid pAN52-NotI (Punt, P. J. et al., Gene 69:49-57, 1988) was digested with NotI and BamHI and the released gpdA promoter of *A. nidulans* was replaced by the NotI and BamHI digested PCR product. The resulting plasmid was named pMLO 133.

```
The PCR primers for the cloning of the cbh2 promoter:

SphI    NotI   +promoter
1. 5' ACATGCATGCATGCGGCCGCGGTTTGTTGCCGTAACCATTCTGTCTCCT 3'   (Sequence ID. No. 7)

XbaI    BamHINcol-1
2. 5' GCTCTAGAGCGGATCCATGGTGCAATACACAGAGGGTGATCTTACAAG 3'    (Sequence ID. No. 8)
```

3. Construction of Vectors for Expression on β-xylosidase

The BamHI fragment containing the protein coding region of the bxl1 gene was released from the plasmid pMLO135 and inserted inbetween the gpdA promoter and trpC terminator of the plasmid pAN52-NotI and inbetween cbh2 promoter and trpC terminator of the plasmid pMLO133. From the resulting plasmids pMLO136 and pMLO137 the β-xylosidase expression casette can be released with NotI and XbaI.

4. Transformation

Both pMLO136 and pMLO137 were cut with NotI and XbaI, gel purified and both fragments were together transformed into *T. reesei* RutC-30 using either acetamide selection or hygromycin selection.

EXAMPLE 2 xdh1 Disruption Construct with Short cDNA Flanking Regions for Integration into the xdh1 locus The xdh1 cDNA -containing plasmid B1073 (FIG. 1.) was prepared as follows. The xdh gene of *Trichoderma reesei* was derived from the cDNA library constructed in the vector pAJ401 (Salobeimo A., et al., Mol. Microbiol. 13, 219-228, 1994), where the cDNA is ligated between the PGK1 promoter and terminator. Poly(A)+mRNA was isolated from *T. reesei* Rut-C30 cultivated on medium containing several plant polysaccharides (Ståhlbrand H., et al., Appl. Environ, Microbiol. 61, 1090-1097, 1995). The cDNA was synthesised using the ZAP-cDNA synthesis kit (Stratagene, Calif., USA) and was ligated into the plasmid pAJ401 (Margolles-Clark E., et al., Appl. Environ. Microbiol. 62, 3840-3846, 1996). A 540 bp SalI-XhoI fragment from B1073 was ligated to XhoI cut pARO21 (Saloheimo et al. 2000, J. Biol. Chemistry 275, 8: 5817-5825), downstream of the pki promoter-hph-cbh2 terminator cassette conferring hygromycin resistance. A clone containing the insert in the desired orientation was isolated and named pM187. The 600 bp 5' xdh1 fragment was excised from B1073 as a EcoRI-PstI fragment. This fragment was made blunt ended using the T4 polymerase and ligated to EcoRV cut pM187 producing pM188, which now has xdh1 5' end downstream of the cbh2 terminator and xdh1 3' end upstream of the pki promoter. The construction of the plasmid pM188 is illustrated in FIG. 2.

pM188 cut with Asp718-SmaI, the fragment containing the disruption cassette was isolated from gel and transformed to *Trichoderma reesei* Rut-C30 strain (Penttilä et al., Gene 61: 151-164, 1987) using hygromycin B selection.

Isolation of the Chromosomal Copy of the xdh1 Gene

The xdh1 cDNA was $^{32}P$ labelled and used as a probe to isolate the chromosomal copy from the genomic cosmid library of *T. reesei* [Mäntylä et al. (1992) Curr. Genet. 21: 471-477]. The library was screened using standard methods and cosmids were isolated from colonies giving a positive hybridisation signal. One of the clones was named pM185. The cosmid was cut with various restriction enzymes and the samples were subjected to Southern blot in order to identify fragments containing the xdh1 gene. The 2.2 and 1.7 kb PstI fragments, both giving a positive hybridisation signal, were cloned into PstI cut pZErO-1 vector and named pM194 and pM193, respectively.

xdh1 Disruption Construct with Chromosomal Flanking Regions for Integration into the xdh1 locus pM193 was cut with EcoRV-XhoI and the 1.5 kb fragment was isolated and made blunt ended with T4 polymerase and ligated to pM194 linearised with XhoI and also treated with T4 polymerase producing pM195. Thus pM195 contains the 5' PstI fragment and the 3' XhoI-PstI fragment of xdh1 separated by EcoRV and NotI sites. pM195 was digested with NotI-SalI, treated with T4 polymerase and ligated to the 3.2 kb blunt ended SphI-XbaI fragment from p3SR2 [Hynes, M. J., Corrick, C. M. and King, J. A. (1983) Mol.Cell. Biol. 8: 1430-1439] containing the *A. nidulans* amdS gene producing pM196. Thus the 320 bp XhoI-SalI fragment is removed from the xdh1 protein coding region and replaced by the amdS gene in pM196. The construction of the plasmid pM196 is illustrated in FIG. 3.

pM196 was cut with Asp718-XbaI and the 7 kb fragment containing the disruption cassette was gel purified and transformed into *T. reesei* Rut-C30 using acetamide selection.

Screening of the Transformants on xylitol and xylose Plates

The transformants were first purified on solid *Trichoderma* minimal medium (Penttilä M. et al., ibid.) supplemented with either 10 mM acetamide as the sole nitrogen source instead of $(NH_4)_2SO_4$ or with 100 µg/ml hygromycin.

From the transformation made with hygromycin marker, transformants were received after three rounds on selective plates and with acetamidase marker, after two rounds on selective plates. All the transformants were single spore purified by streaking them out on selective media containing plates. Four single spore purified colonies from each transformant were tested on plates containing Trichoderma minimal medium, pH adjusted to 5.5 with KOH and supplemented either with 2% xylitol or 2% xylose as the only carbon source and without any organic nitrogen source. The possible inactivants could be found by the poor growth both on xylitol and especially on xylose containing plates.

The Verification of the Inactivants by Southern Blotting

On xylitol and xylose plates tested xdh1 inactivants containing the hph marker and xdh1 inactivants containing the amdS marker were tested by Southern blotting technique. Fungal DNA was isolated according to Raeder, U. et al. (1985) *Lett. Appl. Microbiol.* 1:17-20. In order to check correct integration of the transformed expression casette into the xdh1 locus 15 µg of DNA of hph transformants was digested with PstI and 15 µg DNA of amdS transformants with XhoI. The DNA fragments were size fractionated in 0.8% agarose gels and blotted onto nylon membrane using standard methods (Maniatis et al., ibid.). Blots were probed with a $^{32}P$-labelled fragment of the xdh1 gene. The probe fragment was digested from plasmid B1073 with the plasmid EcoRI and XhoI and isolated from the gel. The probe was labeled using the Random Primed DNA Labeling Kit (Boehringer Mannheim) and [$\alpha$-$^{32}P$]dCTP (Amersham). Hybridization was done in 50% formamide-5× Denhardt's-5×SSPE-0.1% SDS-100 µg/ml denatured herring sperm DNA-1 µg/ml polyA DNA at 42° C. overnight and washed twice for 5 min in 2×SSC at room temperature and for 30 min in 2×SCC-0.1% SDS at 65° C. An xdh1 inactivant having two copies of the transformation cassette was designated no. 63 and used in further studies.

EXAMPLE 3

Construction of xdh1 Inactivant Overexpressing β-xylosidase

From the plasmid pMLO136 containing the β-xylosidase gene under the gpd promoter and trpC terminator, and from the plasmid pMLO137, containing β-xylosidase under the cbh2 promoter and trpC terminator, the expression cassettes are released by cutting the plasmids with NotI and XbaI digestion. The xdh1 inactivant containing the hph marker will be transformed according to Penttilä et al. (ibid.) either with one or both of the isolated expression cassettes using the plasmid p3SR2 containing an acetamidase gene as a selective marker. The xdh inactivant containing the amdS marker will be transformed similarly either with one or both of the expression cassettes but using the plasmid pRLM$_{EX}$30 [Mach, R. L., Schindler, M. And Kubicek, C. (1994) Genet. 25: 567-570] containing the hph gene as a selective marker.

The construct can be made also by transforming the xdh1 cassette released from the plasmid pM188 which contains the hygromycin gene (described above) to the strain overexpressing β-xylosidase (VTT-D-98694) using hygromycin as a selective marker.

EXAMPLE 4

Production of xylanase and β-xylosidase by Genetically Modified *Trichoderma reesei*

*Trichoderma reesei* VTT-D-98694, derived from *T. reesei* Rut C-30 as described in Example 1, by inserting a homologous β-xylosidase gene into the genome under the control of the cbh2 promoter, was used to study the production of xylanase and β-xylosidase. The microorganism. produces β-xylosidase when induced to produce cellulases, e.g. CBHII. Both the production of xylanase and the production of β-xylosidase are achieved under induction. The parent strain *T. reesei* Rut C-30 was used as a control.

Inoculations of the microorganisms were prepared by growing them in the following medium:

| | |
|---|---|
| Sloka floc cellulose | 20.0 gl$^{-1}$ |
| Wheat based distiller's grain | 10.0 gl$^{-1}$ |
| K$_2$HPO$_4$ | 15.0 gl$^{-1}$ |
| (NH$_4$)$_2$SO$_4$ | 5.0 lg$^{-1}$ |

I 1×200 ml was grown on agar substrate 2 d, 200 rpm, at 29° C.
II 5×200 ml, 1 d, 200 rpm, 29° C.

The fermentation medium was the following:

| | | |
|---|---|---|
| Sloka floc cellulose | 40.0 gl$^{-1}$ → | 600 g |
| Wheat based distiller's grain | 20.0 gl$^{-1}$ → | 300 g |
| K$_2$HPO$_4$ | 5.0 gl$^{-1}$ → | 75 g |
| (NH$_4$)$_2$SO$_4$ | 5.0 gl$^{-1}$ → | 75 g |

The fermentations were carried out by using a 20 l fermentor, Chemab LF 20, containing 14 l fermentation medium and inoculation, made up to 15 l, for four days at a temperature of 29° C., a pH of 6.0-6.5 (regulated by NH$_4$OH and H$_3$PO$_4$), while mixing at about 600 rpm and aerating to keep the level of dissolved oxygen over 30%.

After fermentation, the broths were cooled to under 20° C. and centrifuged in a Cryofuge, 5000 rpm, 20 min, <10° C. The centrifuged broths were concentrated by ultrafiltration to about 1.0-1.5 l.

At various stages of the process samples were taken and the following enzyme activities measured: endoglucanase [HEC, Bailey and Nevalainen (1981) Enzyme Microb Technol 3:153-157., IUPAC (International Union of Pure and Applied Chemistry) (1987) Pure and Appl Chem 59:257-268], xylanase, β-xylosidase, FPU [Filter Paper Unit, Mandels et al., Biotechnol. Bioeng. Symp. 6 (1976) 21-33. John Wiley and Sons, NY., IUPAC (International Union of Pure and Applied Chemistry) Pure and Appl. Chem. 59 (1987) 257-268], acetyl xylan esterase (AXE), α-glucuronidase (αGLU) and α-arabinosidase. In addition, the protein content was determined using the Lowry TCA method. The results obtained at the end of fermentation are presented in Table 1.

The results show that the production of cellulases (HEC, FPU) was rather weak on the cellulose medium used, due to the high pH value. However, the FPU value, 3.1 units ml$^{-1}$, and the protein content, 6.2 gl$^{-1}$, both indicate that there were moderate amounts of cellulases in the broth. The xylanase production was on the expected level [Bailey et al.(1993), Appl. Microbiol. Biotechnol. 40: 224-229]. The β-xylosidase activity shown by the genetically modified strain was about 450 nkat ml$^{-1}$, which result was significantly higher than the result obtained by the parent strain, 32 nkat ml$^{-1}$. The specific activities were 72.6 nkat/g protein and 4.9 nkat/g protein, respectively.

TABLE 1

Protein content and enzyme activities produced after fermentation (92 h)

| Code | Control 00246 | GMO 00241 |
|---|---|---|
| β-xylosidase, nkat/ml | 32 | 450 |
| Xylanase, nkat/ml | 9650 | 9880 |
| protein, g/l | 6.5 | 6.2 |
| AXE, nkat/ml | 103 | 93 |
| FPU, U/ml | 2.6 | 3.1 |
| β-glucanase, nkat/ml | 34 | 35 |
| β-xylosidase, specific activity nkat/g protein | 4.9 | 72.6 |

In conclusion, addition of the β-xylosidase gene resulted in a many-fold increase in β-xylosidase production while the production of other enzymes remained essentially on the original level.

EXAMPLE 5

Production of xylanase and β-xylosidase by Genetically Modified *Trichoderma reesei*

The previous example was repeated by using a different substrate based on lactose and xylan. The two microorganisms were separately grown on the following medium:

| | |
|---|---|
| Lactose | 20.0 g l$^{-1}$ |
| Peptone | 4.0 g l$^{-1}$ |
| Yeast extract | 1.0 g l$^{-1}$ |
| KH$_2$PO$_4$ | 15.0 g l$^{-1}$ |
| (NH$_4$)$_2$SO$_4$ | 2.8 g l$^{-1}$ |
| MgSO$_4$ x 7H$_2$O | 0.5 g l$^{-1}$ |
| CaCl$_2$ x 7H$_2$O | 0.4 g l$^{-1}$ |
| Mineral solution | 1.0 ml l$^{-1}$ |
| Mineral solution: | |
| FeSO$_4$•7H$_2$O | 5.0 mg/l |
| MnSO$_4$•H$_2$O | 1.6 mg/l |
| ZnSO$_4$•7H$_2$O | 1.4 mg/l |
| CoCl$_2$•6H$_2$O | 3.7 mg/l | and the inoculations were prepared as described in the previous example.

The fermentation medium was the following:

| | | |
|---|---|---|
| Lactose | 40.0 g l$^{-1}$ → | 600 g |
| Peptone | 4.0 g l$^{-1}$ → | 60 g |
| Yeast extract | 1.0 g l$^{-1}$ → | 15 g |

-continued

| | | | |
|---|---|---|---|
| $KH_2PO_4$ | 4.0 g l$^{-1}$ | → | 60 g |
| $(NH_4)_2SO_4$ | 2.8 g l$^{-1}$ | → | 42 g |
| $MgSO_4 \times 7H_2O$ | 0.6 g l$^{-1}$ | → | 9 g |
| $CaCl_2 \times 2H_2O$ | 0.8 g l$^{-1}$ | → | 12 g |
| Mineral solution | 2.0 ml l$^{-1}$ | → | 30 ml |

In addition, 2.0 l of Stake-xylan solution, Cultor (see example 6), as a 1:2 dilution was fed with a MSC-WW5 pump, Chemap, hose 4/7 mm. The feed was started after a growth period of about 8 h. During the first 24 h, the feed rate was about 30 mlh$^{-1}$, thereafter about 40 mlh$^{-1}$.

The fermentations were carried out using a 20 l fermentor, ChemabCF 2000 containing 14 l fermentation medium and inoculation, up to 15 l, for four days at a temperature of 29° C., a pH of 4.0-5.0 (regulated by $NH_4OH$ and $H_3PO_4$), while mixing (500-800 rpm) and aerating to keep the level of dissolved oxygen over 30%. After fermentation, the broths were processed and samples taken as described in the previous example.

The results obtained at the end of fermentation are shown in Table 2.

TABLE 2

Protein content and enzyme activites produced after fermentation (92 h)

| | Induced Stake-liquor | |
|---|---|---|
| Code | Unmodified Rut-30 990006 | Recomb. Rut-30 990002 |
| β-xylosidase, nkat/ml | 210 | 960 |
| Xylanase, nkat/ml | 12100 | 12150 |
| protein, g/l | 7.8 | 9 |
| AXE, nkat/ml | 325 | 315 |
| FPU, U/ml | 4.2 | 3.6 |
| β-glucanase, nkat/ml | 7.2 | 19 |
| β-xylosidase, specific activity nkat/g protein | 27 | 106 |

The production of both xylanase and, in particular, β-xylosidase was significantly higher as compared to the previous example. In this connection, it is worth pointing out that these examples describe preliminary tests and thus, by systematic optimisation of different parameters, such as fermentation medium composition and xylan feed, much better yields can be obtained. The example clearly shows that a soluble lactose-xylan medium provides better results than the cellulose-based medium used in the previous example. The xylo-oligosaccharide solution has been an efficient inducer both for the production of cellulases and, in particular, of native β-xylosidase. Again, the parent strain produces significantly less, about 22%, β-xylosidase than the genetically modified organism. In this induced fermentation process condition the specific activity of β-xylosidase was 106 nkat/g protein for the genetically modified microorganism and 27 nkat/g protein for the parent strain. A more than five-fold increase in β-xylosidase production gives significantly better yields in the ultimate hydrolysis processes.

EXAMPLE 6

Hydrolysis Efficacy of the Enzymes Produced by Genetically Modified *Trichoderma reesei*

The aim of this study was to test the efficacy of the enzymes produced by the genetically modified *Trichoderma reesei* for the hydrolysis of xylo-oligomer raw materials like steam exploded birch wood extract (Stake-liquor).

A steam exploded birch wood extract was produced by Cultor and stored at a concentration of 32%. The composition of the Stake-liquor was the following:

| | | After acid hydrolysis (1 h, 120° C., pH1) |
|---|---|---|
| Dry solids | 33.8% (RI*), | 28% (in oven, 105° C., 24 h) |
| Oligosaccharides | 62% DS (RI) | |
| Xylose | 10% DS (RI) | 60.6% |
| Galactose + rhamnose | 1.1% DS (RI) | 3.75% |
| Arabinose + mannose | 1.9% | 5.6% |
| Glucose | | 3.1% |
| pH | 3.6 | |
| Color (Icumsa) | 86 500 | |
| Conductivity | 3600 uS/cm | |

*RI = Refractometry Index

Four different enzymes were produced in pilot fermentation as described above. Codes and analysis of the enzymes produced by the genetically manipulated *Trichoderma reesei* and by the unmodified parent strain with and without induction with Stake-liquor are those disclosed in Tables 1 and 2.

Multifect GC-140, Genencor Intern. Europe, Jämsänkoski, Finland, was used as a commercial reference. Analysis of Multifect XK 803 showed a protein content of 82 g/l (Lowry), a β-xylosidase activity of 600 nkat/ml, and a xylanase activity of 780000 nkat/ml.

Enzymatic hydrolysis of xylo-oligosaccharides or xylan was carried out at a concentration of 4%, which has been proved to be the level where end product inhibition of xylose is at a tolerable level. The hydrolysis was carried out at 45° C., agitating 100 rpm, initial pH 4.5 and hydrolysis time 24-48 h. The dosage of enzymes, as β-xylosidase, varied between 12-150 nkat/g of d.s. of Stake-liquor.

The carbohydrates of the hydrolysate were analysed with an HPLC apparatus equipped with a RI-detector on a column in $Pb^{++}$-form at 65° C., flow rate 0.4 ml/min, injection volume 20 μl, with water as the mobile phase. The hydrolysis yields were calculated from the detected monomeric carbohydrates.

The enzymatic conversion of xylo-oligosaccharides in Stake-liquor with the tested enzymes is shown in table 3. All the enzymes produced rather equal amounts of xylose from Stake-liquor when comparing the efficiency as β-xylosidase activity used per g dry solids. The commercial enzyme Multifect XS 803 was much more efficient at the same β-xylosidase level than the test enzymes because Multifect XS 803 contained a higher amount of xylanase, which has also a strong contribution to the degradation of xylooligosaccharides.

The efficacy of the enzyme preparates was compared also by making calculations based on the amount of enzyme (with an equal protein content) which was required to achieve the same hydrolysis level. With this type of calculation the raw materials used for fermentation of the enzyme preparation are at an almost equal level. The amount of an individual enzyme solution of each test enzyme preparation used for hydrolysis was converted to the amount of enzyme (liter/ton dry solids), which corresponded to enzyme at a protein level of 45 g/l. The reference level of 45 g protein/l was chosen to be the same as the level of protein in Genencor's commercial hemicellulase Multifect GC-140. The results calculated on the protein level 45 g/l are shown in table 3.

According to Table 3 the enzymes produced by the recombinant *T. reesei* strains are clearly beneficial when comparing the hydrolysis of Stake-liquor to xylose on the basis of required amount of enzyme protein.

TABLE 3

Xylose yields obtained from Stake-liquor (Dosage of enzymes was converted to the protein level 45 g/l)

| Dosage converted to 45 g prot/l l/ton D.S. | Dosage as β-xylosidase nkat/g D.S. | Xylose yield after 21 h %/D.S. | after 44 h %/D.S. |
|---|---|---|---|
| 1) Recomb Rut-30 + inducer MFCS 990002 | | | |
| 38 | 150 | 54.3 | 57.2 |
| 19 | 75 | 49.5 | 55.3 |
| 6 | 25 | 33.2 | 45.9 |
| 3 | 12.5 | 24.1 | 35.4 |
| 2) Rut-30 + inducer MFCS 990006 | | | |
| 101 | 150 | 54.2 | 58.2 |
| 51 | 75 | 51.2 | 54.4 |
| 17 | 25 | 33.0 | 45.9 |
| 8 | 12.5 | 23.6 | 32.4 |
| 3) Recomb Rut-30 00246 | | | |
| 38 | 150 | 53.7 | 54.0 |
| 19 | 75 | 51.9 | 51.6 |
| 6 | 25 | 32.9 | 43.3 |
| 3 | 12.5 | 23.0 | 30.9 |
| 4) Rut-30 00246 | | | |
| 478 | 150 | 57.4 | 56.8 |
| 239 | 75 | 53.4 | 56.0 |
| 80 | 25 | 38.3 | 48.8 |
| 39 | 12.5 | 27.5 | 38.0 |
| 5) Multifect XK 802 | | | |
| 456 | 150 | 60.7 | 60.2 |
| 228 | 75 | 56.7 | 59.5 |
| 76 | 25 | 48.3 | 54.8 |
| 36 | 12.5 | 38.1 | 49.6 |
| Feed solution (no enzyme addition) | | 10.9 | |
| Max. xylose yield (after acid hydrol.), % on D | | 60.6 | |

The enzymes produced by the recombinant *T. reesei* strains are the most efficient ones to hydrolyse Stake-liquor to xylan. The combination of recombinant strain and inducer did not improve the hydrolysis efficiency of protein significantly (Table 4) as compared to the enzyme protein produced by the recombinant strain without inducer. Both enzymes have very similar specific β-xylanase activity but rather high differences in specific acetylesterase activity. Probably the high β-xylosidase content compensates for the importance of acetyl esterase. However, the improved efficiency of the enzyme product produced with the inducer is probably partly due to the higher acetylesterase content when comparing the enzymes produced by the unmodified strains. A summary of the results is shown in Table 4 wherefrom it can be seen that the amount of enzyme produced by the recombinant strain, which is required to hydrolyse 85% of xylo-oligosaccharides to xylose, is only ⅙-⅛ of the amount of the enzyme produced by the unmodified parent strain.

TABLE 4

Enzyme dosage (per 45 g protein/l) required to obtain a xylose yield of 85% (= 51.5% of D.S.) from xylo-oligosaccharides of Stake-liquor.

| 85% yield | Dosage of enzyme containing 45 g prot/l as l/ton D.S. | |
|---|---|---|
| | in 21 hours | in 44 hours |
| Recomb. Rut 30 + inducer, VTT990002 | 24.5 | 12 |
| Recomb. Rut 30, VTT00241 | 19 | 19 |
| Rut 30 + inducer, VTT990006 | 54 | 35 |
| Multifect XS 803 | 120 | 50 |
| Rut 30, VTT00246 | 170 | 115 |

EXAMPLE 7

Production of xylitol in Shake Flask Cultivations on Lenzing xylan with xdh1 Inactivant and the Host Strain RutC-30

Xdh1 inactivant 63 and host strain RutC-30 were cultivated at 200 rpm at 28° C. in 2 l shake flasks (200 ml of culture medium) on buffered *Trichoderma* minimal medium (Penttilä et al., ibid.) at pH 5.5 supplemented with 3% Lenzing xylan and 0.2% proteose peptone. 200 ml of growth medium in 2 l shake flask was inoculated with $1.2 \cdot 10^8$ spores. Samples were taken from the shake flasks after 3, 4, 5, 6 and 10 days.

Xdh1 inactivant and RutC-30 were cultivated similarly on buffered *Trichoderma* minimal medium at pH 5.5 supplemented with 3% Lenzing xylan, 0.2% proteose peptone and 2% lactose as a cosubstrate. Samples were taken as described above.

Supernatant samples were separated by filtering through a GF/B glass fibre filter (Whatman) and stored at −20° C. The mycelia were washed with sterile water and stored at −70° C.

The amount of xylitol, xylose, lactose and glucose were analysed from the supernatant samples by HPLC with HPX-87H column (Pharmacia) flow rate 0.3 ml/min. The amount of xylitol was confirmed with Cobas MIRA Plus (Roche Diagnostic Systems) using the D-Sorbitol/Xylitol kit (Boehringer Mannheim, Cat. no 670 057), lactose with Lactose/D-Galactose kit (Boehringer Mannheim, Cat. no 176 303) and glucose with Glucose/GOD-Perid Method (Boehringer Mannheim, Cat. no MPR 3 124 036).

In order to simulate the production of xylitol with a strain overexpressing β-xylosidase and having its xylitoldehydrogenase activity inactivated, purified and concentrated β-xylosidase enzyme (290 nkat/ml) was added to the medium described above. The cultivations were carried out as described above in shake flasks with the xdh disruptant and the parent strain RutC-30 for 10 days on minimal medium containing Lenzing xylan as the sole carbon source and peptone as the organic nitrogen source with and without addition of purified β-xylosidase, lactose or both.

The xdh inactivant grew and consumed xylose slower than the parent strain on the media used. After consuming both xylose and lactose (after 4-5 days) both strains began to use the xylitol in the culture medium. On pure xylan without any additions the amount of xylitol produced by the inactivant was 1.3 g/l after 4 days. If lactose was added, the amount increased to 2.0 g/l. With the addition of β-xylosidase the amount increased to 1.4 g/l. However, if both lactose and β-xylosidase were added at the beginning of the cultivation, the amount of xylitol could increase up to 4.9 g/l which confirms that by overexpressing β-xylosidase the production of xylitol can be improved. The maximum amount of xylitol produced by the parent strain RutC-30 was 0.3 g/l.

As a summary, on the xylan based media the best production of xylitol (4.9 g/l) could be achieved when both β-xylosidase and lactose were added to the medium. The inactivant produced around 20-fold more xylitol than the parent strain RutC-30. The yield was 0.17 g xylitol/g xylan and 0.273 g xylitol/g dry weight. The addition of β-xylosidase increased the amount of xylitol produced 3.3-fold on that particular medium.

The results are summarised in Table 5A.

EXAMPLE 8

Production of xylitol in Shake Flask Cultivations on xylose, arabinose and a Mixture of xylose and arabinose with xdh1 Inactivant and the Host Strain, with and without Daily Addition of glucose Xdh1 inactivant 63 and host strain RutC-30 were cultivated at 200 rpm at 28° C. in 2 l shake flasks (300 ml of culture medium) on buffered *Trichoderma* minimal medium (Penttilä et al., ibid.) at pH 5.5 supplemented with either 3% xylose, 3% arabinose or a mixture of 1.5% xylose and 1.5% arabinose, and 0.2% proteose peptone and 0.2% glucose. 300 ml of growth medium in a 2 l shake flask was inoculated with $1.8 \cdot 10^8$ spores. Samples were taken from the shake flasks after 2, 3, 4, 5, 6, 7, 10 and 14 days.

Xdh1 inactivant and RutC-30 were cultivated similarly on buffered *Trichoderma* minimal medium at pH 5.5 supplemented with either 3% xylose, 3% arabinose or a mixture of 1.5% xylose and 1.5% arabinose, and 0.2% proteose peptone and 0.2% glucose as a cosubstrate. In addition glucose was added daily to the final concentration 0.2%. Samples were taken as described above.

Supernatant samples were separated by filtering through GF/B glass fibre filter (Whatman), and stored at −20° C. The mycelia were washed with sterile water and stored at −70° C.

The amount of xylitol, xylose, arabinose and glucose were analysed from the supernatant samples by HPLC with HPX-87H column (Pharmacia) flow rate 0.3 ml/min. The xylitol amount was confirmed with Cobas MIRA Plus (Roche Diagnostic Systems) using the D-Sorbitol/Xylitol kit (Boehring Mannheim, Cat. No 670 057), arabinose with Lactose/D-Galactose kit (Boehringer Mannheim, Cat. No 176 303) and glucose with Glucose/GOD-Perid Method (Boehringer Mannheim, Cat. no MPR 3 124 036).

Simulation of using an xdh inactivant overexpressing β-xylosidase is carried out as described in Example 7.

The inactivant grew much slower on xylose than the host strain but it grew even more slower on arabinose. Daily addition of glucose improved the growth but nevertheless the inactivant was slower in growth as well as in the consumption of xylose and arabinose. The host strain had consumed both the xylose and arabinose after 5 days, but it took 6-7 days for the inactivant to consume the xylose and even 14 days to consume the arabinose if glucose was not added. The addition of glucose daily increased the amount of the mycelia and enhanced especially the consumption of arabinose. Xylitol was produced in an amount of 4.4 g/l on pure xylose medium, 5.3 g/l on pure arabinose and about 4.1 g/l on the mixture of xylose and arabinose. This indicates that *Trichoderma* is capable of producing xylitol from arabinose as well. Because of the slow consumption rate of arabinose it seems that the conversion efficiency from arabinose to xylitol is better than from xylose to xylitol. The xylitol produced is consumed when all the other carbon sources have been depleted. If glucose was fed daily, the production of xylitol could be increased slightly to 5.0 g/l on xylose, to 5.1 g/l on arabinose and to 4.2 g/l on the mixture of xylose and arabinose. Since glucose was present in the medium because of daily addition, the xylitol produced was not consumed during the cultivation.

The results are summarised in Table 5B.

TABLE 5

Production of xylitol with xdh inactivated *T. reesei*

| | | Cell dry weight/g/l | | Production of xylitol, g/l | |
|---|---|---|---|---|---|
| | Growth medium | Control RUT C-30 | xdh inactivated 63 | Maxim. values RUT C-30 | xdh inactivated 63 |
| A | Lenzing xylan | dw g/l | | | |
| | 3% xylan + 2% lactose + β-xylosidase + 2% xylitol | 22 (5 d) | 15 (5 d) | 15 (5 d) | 23 (5 d) |
| | 3% xylan + 2% lactose + β-xylosidase | 21 (5 d) | 18 (5 d) | 0.2 (4 d) | 4.9 (5 d) |
| | 3% xylan + β-xylosidase | 14 (4 d) | 13 (5 d) | 0.1 (3 d) | 1.4 (4 d) |
| | 3% xylan + 2% lactose | 15 (5 d) | 11 (5 d) | 0.3 (3 d) | 2 (5 d) |
| | 3% xylan | 11.5 (4 d) | 11 (5 d) | 0.2 (3 d) | 1.3 (4 d) |
| B | 3% xylose | 10 g/l (4 d) | 8.5 (6 d) | 0.1 (4 d) | 4.4 (7 d) |
| | 3% arabinose | 10 (6 d) | 8 (12 d) | 0.06 (4 d) | 5.3 (10 d) |
| | 1.5% arabinose + 1.5% xylose | 10 (5 d) | 9 (7 d) | 0.01 (6 d) | 4.1 (6 d) |
| | 3% xylose + 0.2% glucose | 16 (7 d) | 10 (7 d) | 0.12 (6 d) | 5.0 (6 d) |
| | 3% arabinose + 0.2% glucose | 17 (10 d) | 12 (10 d) | 0.05 (6 d) | 5.4 (7 d) |
| | 1.5% + 1.5% + 0.2% glucose | 13 (7 d) | 11 (10 d) | 0.01 (7 d) | 4.2 (7 d) |
| C | 8% xylose + glucose | | 19.2 (15 d) | | 14.5 (15 d) |
| | 8% xylose | | 17.2 (13 d) | | 14.5 |
| | 8% arabinose + glucose | | 17.8 (15 d) | | 20.4 (13 d) |
| | 8% arabinose | | 23 I (15 d) | | 4.7 (13 d) |

When cultivating either on pure xylose or arabinose the best production was received when cultivating on xylose with glucose feed (5.0 g/l).

EXAMPLE 9

Production of xylitol in Shake Flask Cultivations on Higher Concentrations of xylose, arabinose with xdh1 Inactivant, with and without Daily Addition of glucose Xdh1 inactivant 63 was cultivated at 200 rpm at 28° C. in 2 l shake flasks on a buffered *Trichoderma* minimal medium (Penttilä et al., ibid.) at pH 5.5 supplemented with 4% lactose and 0.2% proteose peptone. 300 ml of growth medium in a 2 l shake flask was inoculated with $1.8 \cdot 10^8$ spores. The mycelia of the inactivant were collected after 6 days of cultivation by centrifuging for 5 minutes at 3000 rpm and transferred to fresh 300 ml buffered *Trichoderma* minimal medium pH 5.5 in a 2 l shake flask supplemented with either 10% xylose or 10% arabinose, and 0.2% proteose peptone and 0.2% glucose. After addition of mycelia the concentration of xylose or arabinose was around 8%. The inactivant was cultivated at 200 rpm at 28° C. Samples were taken from the shake flasks after 1, 2, 3, 4, 6, 7, 8, 9, 10 and 15 days.

The Xdh1 inactivant was cultivated similarly on buffered *Trichoderma* minimal medium at pH 5.5 supplemented with either 8% xylose, 8% arabinose and 0.2% glucose as a cosubstrate. In addition glucose was added daily to the final concentration 0.2%. Samples were taken as described above.

Supernatant samples were separated by filtering through a GF/B glass fibre filter (Whatman) and stored at –20° C. The mycelia were washed with sterile water and stored at –70° C.

The amount of xylitol, xylose, arabinose and glucose were analysed from the supernatant samples by HPLC with HPX-87H column (Pharmacia) flow rate 0.3 ml/min. The xylitol amount was confirmed with Cobas MIRA Plus (Roche Diagnostic Systems) using the D-Sorbitol/Xylitol kit (Boehring Mannheim, Cat. No 670 057), arabinose with Lactose/D-Galactose kit (Boehringer Mannheim, Cat. No 176 303) and glucose with Glucose/GOD-Perid Method (Boehringer Mannheim, Cat. no MPR 3 124 036).

The results are summarised in Table 5C.

EXAMPLE 10

Production of xylitol in Shake Flask Cultivations on L-arabitol with the xdh1 Inactivant and the Host Strain, with and without Daily Addition of glucose L-arabitol is the next compound from arabinose in the metabolic pathway from L-arabinose to xylitol. In order to see whether L-arabitol is converted to xylitol as efficiently in the inactivant 63 and Rut-C30 were grown on 3% L-arabitol with and without 0.2% glucose feed.

Xdh1 inactivant 63 and host strain Rut-C30 were first cultivated at 200 rpm at 28° C. in 2 l shake flasks on buffered *Trichoderma* minimal medium at pH 5.5 supplemented with 4% lactose and 0.2% proteose peptone. 300 ml of growth medium in a 2 l shake flask was inoculated with $1.8 \cdot 10^8$ spores. The mycelia of the inactivant were collected after 6 days cultivation and of Rut-C30 after 5 days cultivation by centrifuging 5 minutes at 3000 rpm, and transferred to fresh 300 ml buffered *Trichoderma* minimal medium pH 5.5 in a 2 l shake flask. The medium was supplemented with 3% L-arabitol, 0.2% proteose peptone and 0.2% glucose as a cosubstrate.

The inactivant grew on both media even though in the beginning of the cultivation the growth was slower as compared to the host strain Rut-C30. Rut-C30 also consumes L-arabitol much quicker than the inactivant. Xylitol is converted from L-arabitol even though not as efficiently as from L-arabinose. The yields and productivities are also slightly lower.

The results are presented in Table 6. The yields (g xylitol/g arabitol) and productivities (mg xylitol/g cell dry weight per hour) are calculated from parallel flasks from the exponential growth phase. The amount of arabitol corresponds to the amount left in the medium after the exponential growth phase.

TABLE 6

Production of xylitol with xdh inactivated *T. reesei*

| Medium | Amount of xylitol (g/l) | Amount of L-arabitol (g/l) | Yield | Productivity (mg/g h) |
| --- | --- | --- | --- | --- |
| 3% L-arabitol + glucose feed | 3.3/3.4 | 3.4/0.9 | 0.11/0.12 | 1.5/1.6 |
| 3% L-arabitol | 3.9/3.4 | 4.3/2.8 | 0.15/0.13 | 2.3/1.6 |

EXAMPLE 11

Production of xylitol in Fed Batch-fermentations

The inactivant 63 was grown in a fermentor as a fed-batch cultivation. The fermentor used was BioFlo IV A, working volume 4 liters, and with automatic control of dissolved oxygen concentration (DO>20%), temperature (29° C.) and pH (between 4.0 and 5.0, controlled by NaOH and $H_3PO_4$). Aeration was 5 l/min and agitation between 400-800 rpm (dependent of the level of DO).

The inoculum was cultivated in shake flasks (2×200 ml) for 3 days at 29° C. at 200 rpm on the medium containing glucose 20 g/l, peptone 4 g/l, yeast extract 1 g/l, $KH_2PO_4$ 15 g/l, $(NH_4)_2SO_4$ 2.8 g/l, $MgSO_4 \times 7\ H_2O$ 0.6 g/l, $CaCl_2 \times 2\ H_2O$ 0.8 g/l, $FeSO_4 \times 7\ H_2O$ 0.005 g/l, $MnSO_4 \times H_2O$ 0.0016 g/l, $ZnSO_4 \times 7\ H_2O$ 0.0014 g/l, $CoCl_2 \times 6\ H_2O$ 0.0037 g/l.

The strain was cultivated in a fermentor first on the similar medium (2% glucose) as in the shake flasks except that only 4 g/l of $KH_2PO_4$ was used. After 22 hours, when the glucose has been consumed, a first batch of xylose was added to the broth (6% xylose in the broth) and the glucose feed was started (0.1 g/l /h, which was about 10% of the glucose consumption rate in the beginning of the cultivation). After 71.5 hours, a second batch of xylose was added and the glucose feed was increased up to 0.25 g/l/h. A third batch of xylose was added after 99 hours, as well as other medium components (nutrients, nitrogen). The rate of glucose feed was not changed. After 142 h a final batch of xylose was added, but no other components, in order to study how efficient the conversion from xylose to xylitol is when the fungus is not able to grow any more. The cultivation was finished after 286 hours.

Supernatant and mycelium samples were treated as in the shake flask cultivations.

In the end of the cultivation, the amount of xylitol was 20.9 g/l. The results are presented in Table 7.

TABLE 7

Xylitol production, xylose consumption, yields (g xylitol/g xylose) and productivities (mg xylitol/g cell dry weight per hour) in different time periods during the cultivation

| Time period of the cultivation | Amount of xylitol produced (g/l) | Amount of xylose consumed (g/l) | Yield | Productivity (mg/g h) |
|---|---|---|---|---|
| 22.5-71.25 h | 3.4 | 39.6 | 0.07 | 4.8 |
| 71.5-99 h | 6.1 | 16.4 | 0.24 | 12.8 |
| 99.25-141.8 h | 3.9 | 28.6 | 0.03 | 2.5 |
| 142-286 h | 20.9 | 44.5 | 0.46 | 8.7 |

EXAMPLE 12

Testing of Possible Inhibiting Effect of xylitol on β-xylosidase 300 nkat concentrated β-xylosidase was incubated with 0, 1, 5, 10, 50, 100, 200 and 300 g/l of xylitol at 28° C. Samples were taken after 0, 0.5, 1, 2, 4, 6, 8, 24, 48 and 72 hours incubation and stored at −20° C. The activity of β-xylosidase was measured as described in Poutanen and Puls (1988) Appl. Microbiol. Biotechnol. 28:425-432. The activity of β-xylosidase remained stable in all the samples taken and thus it is not inhibited by xylitol.

EXAMPLE 13

Reduction of arabinose to arabinitol

Purified arabinose syrup is hydrogenated to arabinitol at elevated temperature and pressure, using Raney nickel (Degussa BK 113 W) as a catalyst. Arabinose syrup is purified with ion exchange resins for demineralisation and decolourisation. The ion exchange resins in the purification process are strongly acidic cation and weakly basic anion resins. The hydrogenation is accomplished in the following conditions: temperature 110° C., pressure 40 bar, catalyst load ten weight percent wet catalyst of sugar dry matter and reaction time is two hours. The concentration of feed arabinose syrup is 65 g/100 ml and conversion of arabinose to arabinitol in hydrogenation is about 99%.

EXAMPLE 14

Chromatographic Separation of xylitol and arabinitol

A 50:50 mixture of xylitol and arabinitol is subjected to chromatographic separation to purify both components. The separation is made in a pilot scale separation column as a batch process. A strongly acid cation exchange resin in calcium form (Finex CS11GC) is used as stationary phase and pure ion exchanged water as eluent. The cross linkage degree of the resin is 5.5% of DVB and the average particle size 0.35 mm. Separation temperature is 65° C. The diameter of the column is 0.225 m and the resin bed height about 5.2 m. The chromatographic separation is performed as follows.

Step 1

Ten liters of feed solution is introduced to the top of the resin bed through a heat exchanger. Feed concentration is 35 g/100 g. The column and the feed solution has a temperature of 65° C.

Step 2

The feed is eluted downwards in the column by feeding ion exchanged eluent water to the top of the resin bed. Temperature is again 65° C. The linear flow rate is 0.75 m/h.

Step 3

The outflow of the column is monitored continuously by on-line density and conductivity measurement device. The outflow is divided into three fractions. Arabinitol is collected in the front of the profile, xylitol from the back. A recycle fraction is introduced between the two product fractions to maintain a high yield for both components.

The concentration (based on refractive index) of all fractions is measured and the composition analyzed with HPLC. Table 8 presents the composition of the three fractions and the feed. The recycle fraction is not considered when calculating the recovery of arabinitol and xylitol.

TABLE 8

Composition of chromatographic fractions

| Fraction | Feed | Arabinitol | Recycle | Xylitol |
|---|---|---|---|---|
| Dry substance, kg DS | 4.0 | 1.6 | 0.8 | 1.6 |
| Concentration, g/100 g | 35 | 13 | 17 | 13 |
| Arabinitol purity, % on DS | 50 | 90 | 50 | 10 |
| Arabinitol yield, % | — | 90 | — | 10 |
| Xylitol purity, % on DS | 50 | 10 | 50 | 90 |
| Xylitol yield, % | — | 10 | — | 90 |

The invention claimed is:

1. A method for the production of xylitol, the method comprising
   (a) providing a genetically modified microorganism, wherein said microorganism is selected from *Trichoderma reesei* and *Trichoderma longibrachiatum*, and said genetic modification comprises inactivation of the xylitol dehydrogenase gene of the microorganism by homologous recombinant technique;
   (b) culturing the microorganism of step (a) in a medium comprising polymer or oligomer materials containing pentose sugars in conditions sufficient for enabling hydrolysis of said polymers or oligomers to xylose and L-arabinose by the microorganism and wherein a compound selected from L-arabinose or L-arabinitol is added to the medium;
   (c) producing xylitol in the microorganism of step (a) by bioconversion of the xylose and L-arabinose obtained in step (b), in an amount at least 10-fold higher than obtained by an unmodified parent strain under the same conditions, and
   (d) recovering said xylitol produced.

2. The method of claim 1, wherein the microorganism used possesses cellulolytic activity.

3. The method of claim 1, wherein the genetic modification reduces the xylitol metabolism in said microorganism.

4. The method of claim 1, wherein the genetic modification further comprises deletion or inactivating of a gene encoding xylulose kinase.

5. The method of claim 1, wherein the polymer or oligomer material containing pentose sugars belong to a group consisting of lignocellulosic prehydrolysates, pentosan extracted from lignocellulosic material, bagasse, sugar beet pulp, corn cobs, corn fibers, oat, wheat, barley and rice hulls straw, and hydrolysates thereof.

6. The method of claim 1, wherein L-arabinose is reduced to L-arabinitol, which in turn is converted to xylulose and finally to a mixture of xylitol and L-arabinitol, the produced xylitol is separated and the produced L-arabinitol is recirculated into the process.

7. The method of claim 1, wherein L-arabinose is reduced to L-arabinitol, which is converted to L-xylulose and finally reduced to a mixture of xylitol and L-arabinitol, the xylitol produced is recovered.

8. The method of claim 7, wherein said genetically modified microorganism is a microorganism selected from the group consisting of:
   (a) a microorganism having L-arabinose-reductase activity,
   (b) a microorganism having L-arabinitol-dehydrogenase activity, and
   (c) a microorganism having L-xylulose-reductase activity.

9. The method of claim 8, wherein one microorganism possessing said three enzyme activities is used.

10. The method according to claim 1, wherein the microbiological production of xylitol is performed in a nitrogen-poor medium.

11. The method of claim 1, wherein the microorganism is *Trichoderma reesei*.

12. A method of claim 1, wherein glucose is used as a co-substrate in step(c).

13. A method of claim 1, wherein xylitol is recovered by a technique selected from filtration, ultrafiltration, chromatographic methods and crystallization.

* * * * *